US008692998B2

(12) United States Patent
Gratton et al.

(10) Patent No.: US 8,692,998 B2
(45) Date of Patent: Apr. 8, 2014

(54) APPARATUS AND METHOD FOR LIGHT EMISSION DETECTION FOR IN-DEPTH IMAGING OF TURBID MEDIA (75) Inventors: Enrico Gratton, San Clemente, CA (US); Alexander Dvornikov, Irvine, CA (US); Viera Crosignani, Pasadena, CA (US)

(73) Assignee: The Regents of the University of California, Oakland, CA (US)

( * ) Notice: Subject to any disclaimer, the term of this patent is extended or adjusted under 35 U.S.C. 154(b) by 16 days.

(21) Appl. No.: 13/444,696

(22) Filed: Apr. 11, 2012

(65) Prior Publication Data
US 2012/0257203 A1 Oct. 11, 2012

Related U.S. Application Data (60) Provisional application No. 61/474,206, filed on Apr. 11, 2011.

(51) Int. Cl.
*G01N 21/00* (2006.01)
(52) U.S. Cl.
USPC .......................................................... 356/441
(58) Field of Classification Search
USPC .......................................................... 356/441
See application file for complete search history.

(56) References Cited

U.S. PATENT DOCUMENTS 5,583,342 A * 12/1996 Ichie ........................ 250/459.1

OTHER PUBLICATIONS

Yaroslavsky, Optical properties of selected native and coagulated human brain tissues in vitro . . . , Phys. Med. Biol., 2002, 2059-2073, 47.

Masters, Mitigating thermal mechanical damage potential during two-photon dermal imaging, J. Biomed. Opt., 2004, 1265-1270, 9(6).
Cheong, A Review of the Optical Properties of Biological Tissues, IEEE J. Quantum Electron, 1990, 2166-2185, 26.
Tang, Effect of pulse duration on two-photon excited fluorescence and second harmonic generation in nonlinear optical microscopy, J. Biomed. Opt., 2006, 020501-1-3, 11.
Dunn, Influence of optical properties on two-photon fluorescence imaging in turbid samples, Appl. Opt., 2000, 1194-1201, 39.
Kobat, Deep tissue multiphoton microscopy using longer wavelength excitation, Opt. Express, 2009, 13354-13364, 17.
Cicchi, Contrast and depth enhancement in two-photon microscopy of human skin ex vivo by use of optical clearing agents, Opt. Express, 2005, 2337-2344, 13.
Ji, Adaptive optics via pupil segmentation for high-resolution imaging in biological tissues, Nat. Methods, 2010, 141-147, 7.
Watson, Two-photon imaging with diffractive optical elements, Front. Neural Circuits, 2009, 1-11, 3.

(Continued)

*Primary Examiner* — Tu Nguyen
(74) *Attorney, Agent, or Firm* — Marcus C. Dawes; Daniel L. Dawes (57) ABSTRACT

An apparatus and method for in-depth fluorescence imaging using two-photon fluorescence imaging in turbid media. The apparatus includes a detector which can significantly enhance the use of a detection method that allows to efficiently collect scattered fluorescence photons from a wide area of the turbid sample. By using this detector it is possible to perform imaging of turbid samples, simulating brain tissue at depths up to 3 mm, where the two-photon induced fluorescence signal is too weak to be detected by previous means used in conventional two-photon microscopy. The detector separates the excitation and detection optics which allows a more efficient collection of fluorescence and enhancing the possible imaging depth.

9 Claims, 6 Drawing Sheets
(3 of 6 Drawing Sheet(s) Filed in Color)

(56) References Cited

OTHER PUBLICATIONS

Cha, Shack-Hartmann wavefront-sensor-based adaptive optics system for multiphoton microscopy, J. Biomed. Opt., 2010, 046022-1-10, 15(4).

Denk, Two-Photon Laser Scanning Fluorescence Microscopy, Science, 1990, 73-76, 248.

Theer, Two-Photon Imaging to a Depth of 1000um in Living Brains by use of a Ti:Al2O3 Regenerative Amplifier, Opt. Lett., 2003, 1022-1024, 28.

Theer, On the fundamental imaging-depth limit in two-photon microscopy, J. Opt. Soc. Am., 2006, 3139-3149, 23.

O'Malley, Imaging in Depth: Controversies and Opportunities, Methods Cell Biol., 2008, 95-128, 89.

Gu, Comparison of penetration depth between two-photon excitation and single-photon excitation in imaging through turbid tissue media, Appl. Phys. Lett., 2000, 1551-1553, 77.

Deng, Penetration depth of single-, two-, and three-photon fluorescence microscopic imaging through human cortex structures, Appl. Opt., 2003, 3321-33229, 42.

Gerritsen, Imaging of Optically Thick Specimen Using Two-Photon Excitation Microscopy, Microsc. Res. Tech., 1999, 206-209, 47.

Oh Eim, Two-photon microscopy in brain tissue: parameters influencing the imaging depth, Neurosci. Methods, 2001, 29-37, 11.

Leray, Out-of-focus fluorescence collection in two-photon microscopy of scattering media, Opt. Commun., 2008, 6139-6144, 281.

Botcherby, Scanning two photon fluorescence microscopy with extended depth of field, Opt. Commun., 2006, 253-260, 268.

Combs, Optimization of multiphoton excitation microscopy by total emission detection using a parabolic light reflector, J. Microsic., 2007, 330-337, 228.

Combs, Optimizing multiphoton fluorescence microscopy light collection from living tissue by noncontact total emission detection (epiTED), J. Microsic., 2010, Jun 21.

Flusberg, Fiber-optic fluorescence imaging, Nat. Methods, 2005, 941-950, 2.

Engelbrecht, Enhanced fluorescence signal in nonlinear microscopy through supplementary fiber-optic light collection, Opt. Express, 2009, 6421-6435, 17.

Chia, Microprisms for In Vivo Multilayer Cortical Imaging, J. Neurophysiol., 2009, 1310-1314, 102.

Ayers, Fabrication and characterization of silicone-based tissue phantoms with tunable optical properties . . . , Proc. SPIE, 2008, 687007-1-9, 6870.

Flock, Optical Properties of Intralipid: A Phantom Medium for Light Propagation Studies, Lasers Surg. Med., 1992, 510-519, 12.

Kodach, Concentration Dependent Scattering Coefficients of Intralipid Measured with OCT, OSA Technical Digest, 2010.

Myaing, Fiber-optic scanning two-photon fluorescence endoscope, Opt. Lett., 2006, 1076-1078, 31.

Le Harzic, Rigid and high-numerical-aperture two-photon fluorescence endoscope, Appl. Opt., 2009, 3396-3400, 48.

* cited by examiner

APPARATUS AND METHOD FOR LIGHT EMISSION DETECTION FOR IN-DEPTH IMAGING OF TURBID MEDIA

RELATED APPLICATIONS

The present application is related to U.S. Provisional Patent Application Ser. No. 61/474,206, filed on Apr. 11, 2011, which is incorporated herein by reference and to which priority is claimed pursuant to 35 USC 119.

GOVERNMENT RIGHTS

This invention was made with government support under Grant No. P41-003155 awarded by the National Institutes of Health. The government has certain rights in the invention.

BACKGROUND

1. Field of the Technology

The disclosure relates to the field of the imaging of in-depth tissue, specifically high-resolution in-depth optical imaging of biological tissue.

2. Description of the Prior Art

The imaging in depth of biological tissue by two-photon microscopy has been conducted by various research groups over the last two decades. In all previously known two-photon microscope systems, excitation and fluorescence detection are performed by use of the same microscope objective, which strongly decreases fluorescence detection sensitivity due to limitations in light acceptance angle and surface area from which fluorescence can be collected by objective. In addition, the coupling objectives to detector optics introduce light losses and complexity of the overall optical system.

Since its invention in 1990, two-photon fluorescence microscopy has been widely used to image biological tissues. The near-infrared light that is used to induce two-photon fluorescence can penetrate deeper inside tissue samples, thus allowing for high-resolution imaging of deep tissue layers. Biological tissue is by nature a turbid media, with optical properties characterized by a strong multiple scattering and inhomogeneity of the refractive index. The excitation light that effectively reaches the focal area is attenuated by scattering so that the imaging depth is limited. Light in biological tissue is strongly forward-scattered, and the optical properties of the media can be characterized by the absorption coefficient $\mu_a$, the scattering coefficient $\mu_s$, the anisotropy factor g and the reduced scattering coefficient $\mu'_s = \mu_s(1-g)$. For most biological tissues the value of g is in the range of 0.6-0.95 and $\mu'_s$ is in the range of 5-15 cm$^{-1}$. Some tissue components, such as blood and melanin may have a noticeable absorption at excitation wavelengths. However, the contribution of absorption and its effect on imaging depth is usually negligible for most biological tissues when compared with attenuation by multiple scattering, because of much lower values of the absorption coefficients, for instance, for brain tissue $\mu_a \sim 1$ cm$^{-1}$.

Most of the excitation light focused inside the turbid media is scattered before reaching the focal area. It has been shown previously that the intensity of unscattered (ballistic) photons reaching the focal area decays exponentially with depth, while the intensity of the total amount of light decays approximately as 1/depth. However, only ballistic photons induce two-photon fluorescence, because scattered photons will either miss the focal area or be time-delayed, thus not contributing to two-photon processes. For this reason, two-photon induced fluorescence is localized only in a small (micron scale) focal area inside the sample that allows high-resolution imaging in turbid media. Obviously, an increase in the excitation light power will lead to an increase in achievable imaging depths, because a sufficient amount of unscattered photons can be delivered to the focal area at deeper layers. However at a certain power level the excitation light will induce out-of-focus fluorescence near the sample surface that will mask the fluorescence signal from the focal area and limit the possible imaging depth.

To increase imaging depth in turbid media most of the research reported in the literature was concentrated on methods that allow the delivery of more excitation power to the focal area and consequently increase fluorescence intensity and depth at which fluorescence signal can be detected. The excitation light peak power depends on pulse duration and energy and shorter pulses of higher energy are preferable for two-photon fluorescence imaging. An imaging depth of 1 mm was demonstrated in brain tissue when a regenerative amplifier was used to increase the excitation pulse power. The numerical aperture (NA) of the focusing optics also affects resolution as well as imaging depth and the optimum NA was found to be 0.6-0.8 for imaging at 300 μm depth in tissue phantoms. The use of longer wavelengths for excitation increases the imaging depth due to less scattering of excitation light by the tissue and 1 mm depth was achieved in the imaging of a mouse brain at 1280 nm wavelength. The application of optical clearing agents which are in fact index matching compounds, was shown to double the image depth in a skin tissue sample (from 40 to 80 μm). Another factor that limits imaging depth in tissue is the optical inhomogeneity of the media that leads to a distortion of the excitation light wave-front and degrades imaging performance. To some extent this problem can be corrected by means of adaptive optics.

Another major problem associated with in-depth fluorescence imaging is the harvesting of fluorescence photons. While acquiring images of deep layers, the detected signal decays with depth due to the decrease in number of induced fluorescence photons, as well as the attenuation of fluorescence by multiple scattering and possible absorption. It is obvious that the ability of the imaging system to collect fluorescence photons propagating in turbid sample will strongly affect the imaging depth, thus deeper layers can be imaged with more sensitive fluorescence detectors.

The overall sensitivity also depends on the efficiency of fluorescence collection optics, which for all commercial and experimental two-photon fluorescence microscope systems utilizes an optical setup, where fluorescence is collected by the same microscope objective that is used for excitation. The collection efficiency of this method is very limited by the ability of the microscope objective to collect photons only at a certain angle and from a relatively small area of the sample, thus leaving most of the fluorescence photons undetected. Several previous attempts describe the use of a parabolic mirror to reflect these "missed" photons to the detector and increase the signal gain and imaging performance. Alternatively, optical fibers can be used for fluorescence collection in imaging systems. A relatively narrow acceptance angle of optical fibers limits their ability to collect fluorescence photons, however, the use of an array of optical fibers, especially large-core fibers with high NA~0.5, can be practically efficient. The additional collection of fluorescence photons by a ring of large-core optical fibers surrounding the objective was shown to have the potential to enhance the overall fluorescence collection efficiency by up to 4-fold signal gain.

What is needed is an enhanced fluorescence detection method that allows for efficiently collecting scattered fluorescence photons from a wide area of the turbid sample even when the two-photon induced fluorescence signal is too weak to be detected by means used in conventional two-photon microscopy.

BRIEF SUMMARY

To resolve this problem and others we decided to separate the excitation and detection optics, thus allowing a more efficient collection of fluorescence and enhancing the possible imaging depth. The current detection method and experimental results on imaging in depth in turbid samples with optical properties that simulate brain tissue are presented herein. To our knowledge, the imaging depth in brain tissue is usually limited to a few hundred microns, and the maximum imaging depth reported is about 1 mm. The use of the current detection method described below allowed us to perform imaging in turbid samples with brain-like optical properties at depths up to 3 mm, while the maximum depth at which images could be acquired on the same samples by the state-of-the-art commercial two-photon microscope (Zeiss LSM 710) was limited to about 500 µm.

In another embodiment, it is possible to have a configuration in which the excitation and detection optics are combined in the same unit to perform imaging from the same side of the sample.

The illustrated embodiments of the invention differ from other known art by the method of signal light detection which is used, namely by separation of excitation and detection optics. For detection we use a wide photocathode area photomultiplier tube (PMT) that is capable to collect scattered fluorescence photons from a wide area of the sample surface. By using an index matching compound, we achieve continuity in the refractive index between sample and PMT photocathode to minimize light losses due to reflection. The PMT also has single photon sensitivity.

Fluorescence photons are collected by the microscope objective. The disadvantage is low efficiency of photon collection, because microscope objectives can collect photons only from very narrow sample area and only at certain angle and lose most of the scattered fluorescence photons. Additional light losses are introduced by optics that couples an objective and detector.

Thus, the illustrated embodiments are directed to high resolution in-depth optical imaging of biological tissue. The illustrated method is highly efficient for detection of light which propagates in multiple-scattering media, such as biological tissue. The depth of optical imaging in turbid media for instance by two-photon microscopy, is limited by ability of detection system to detect weak fluorescence signals attenuated by media scattering and absorption. The disclosed detection method allows one to increase imaging depth to a few millimeters deep, compared to a few hundred microns that achieved using conventional detection methods.

The objects of the illustrated embodiments of the invention are achieved by utilizing a wide cathode area photomultiplier tube coupled to waveguide for detection and a shutter with index matching compounds. The detector assembly is placed directly on the specimen. The index matching compounds eliminate or reduce losses due to light reflection at optical component boundaries between the optical elements in the detector assembly. Unlike conventional detection methods that utilize microscope objectives for emission light collection, the illustrated embodiments of the method allow collection of multiply media-scattered photons from a wide area of the sample surface with minimum light losses (e.g. an area 25 mm in diameter or greater), because all photons, which reach the sample surface and enter the detector at any angle are directed to photocathode and detected. This cannot be achieved by use of microscope objectives, which have limited light acceptance angle and area.

In addition to high detection efficiency, the detector is simple in construction and does not require any focusing optics. The purpose of these embodiments is to create a practical imaging system that is capable of obtaining cellular resolution images of biological tissues in depth of more than few millimeters. The advantage of the illustrated embodiments of the invention is the ability of detector to collect multiply scattered photons from a wide area of the turbid media at any entering angle and direct them to PMT photocathode without losses or at least disabilitating losses. Using this detector in a two-photon microscope, the imaging depth of tissue samples can be expended to few millimeters (1-3 mm), compared with conventional detection that allows imaging only up to 1 millimeter. The invention can be used in two-photon microscopy for tissue imaging in depths of few millimeters.

The detector can be combined with a scanning endoscope in the single imaging head to make an imaging device for noninvasive diagnostics and imaging of brain, breast, skin tumors and other disease states.

The current invention provides an apparatus for imaging in depth in a turbid sample. The apparatus includes a source of an excitation beam, excitation optics optically coupled to the excitation beam for optically processing the excitation beam, and a microscope optically coupled with the processed excitation beam. An objective is coupled to the microscope and is disposed on a first side of the turbid sample for directing the coupled excitation beam onto the first side of the turbid sample. A detector assembly is disposed on a second side of the turbid sample, wherein the detector includes detection optics and includes means for producing an in depth image from detected fluorescence coupled to the detector.

In one embodiment, the means of the apparatus for producing an in depth image from detected fluorescence coupled to the detector includes means for producing an image of fluorescence from approximately 1-3 mm deep within the turbid sample.

In one specific embodiment, the detector assembly of the apparatus includes a mirror coated cylinder including a first end and a second end, a photomultiplier tube optically coupled with the first end of the mirror coated cylinder, and a shutter optically coupled with the second end of the cylinder, wherein the shutter further includes a plurality of filters and a selectively movable plate for opening and closing the shutter. The plate of the shutter is disposed between two filters. In a related embodiment, the photomultiplier tube is a wide cathode area photomultiplier tube and is optically coupled to the mirror coated cylinder which functions as a waveguide. The detector assembly further includes an index matching compound between the shutter, filters, mirror coated cylinder and photomultiplier tube photocathode.

In another embodiment, the excitation beam of the apparatus is directed from the objective disposed on the first side of the turbid sample and opposing the detector which is disposed on the second side of the turbid sample.

In yet another embodiment, the detection optics of the detector is disposed directly onto the surface of the turbid sample.

In a separate embodiment, at least a portion of the excitation optics of the apparatus are disposed within the detector assembly itself. The detector assembly includes in this embodiment an optical fiber optically coupled to the objective and extending into the detector assembly, a piezoelectric scanner optically coupled to the optical fiber, and a GRIN lens optically coupled to the piezoelectric scanner. The GRIN lens is arranged and configured within the detector assembly to be disposed directly onto the turbid sample.

The current invention also provides for a method for imaging in depth in a turbid sample. The method includes exciting fluorescence within a turbid sample with a first optical system, detecting excited fluorescence from the sample using a second optical system that is separate from the first optical system, and producing an in depth image of the detected fluorescence.

In one embodiment, producing an in depth image from detected fluorescence includes producing an image of fluorescence from approximately 1-3 mm deep within the turbid sample. The method may also selectively prevent excited fluorescence from entering the second optical system by selectively closing the shutter. In a related embodiment, the method also provides an index matching compound to provide continuity in the refractive index between the sample and the photomultiplier tube to minimize light losses.

In another embodiment, detecting excited fluorescence from the sample using the second optical system includes filtering the excited fluorescence through a plurality of filters included within a shutter, light guiding the filtered fluorescence through a mirror coated cylinder, and collecting the light guided, filtered fluorescence from a wide area of the sample surface using a photomultiplier tube.

In yet another embodiment, exciting fluorescence within the turbid sample includes exciting fluorescence within the turbid sample on the opposing side of the turbid sample from which the excited fluorescence from the sample is detected.

In still a further embodiment, exciting fluorescence within the turbid sample includes exciting fluorescence within the turbid sample on the same side of the turbid sample from which the excited fluorescence from the sample is detected. Exciting fluorescence within the turbid sample on the same side of the turbid sample from which the excited fluorescence from the sample is detected may also include exciting fluorescence in the turbid sample using excitation optics disposed within a detector assembly.

In yet a separate embodiment, detecting excited fluorescence from the sample includes filtering the excited fluorescence through a filter disposed in one end of the cylinder, light guiding the excited fluorescence through a mirror coated cylinder, and collecting the light guided, filtered fluorescence from a wide area of the sample surface using a photomultiplier tube photocathode.

Finally, in one embodiment detecting excited fluorescence from the sample using a second optical system includes detecting excited fluorescence using unfocussed optics.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

BRIEF DESCRIPTION OF THE DRAWINGS

The specification contains at least one drawing executed in color. Copies of this patent or patent application publication with color drawing(s) will be provided by the Office upon request and payment of the necessary fee.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

Turbid samples were first prepared by dispersion of fluorescent microspheres (Invitrogen FluoSpheres yellow-green, size 1 um or 15 um) and $TiO_2$ particles (Atlantic Equipment Engineers, Ti-602) as a scattering agent in a gelatin or agar gel. Gelatin (Sigma-Aldrich) or agar (Fisher Scientific) was dissolved in hot water to make a 5% or 1% solution respectively, to which fluorescent microspheres and $TiO_2$ powder were subsequently added. The mixture was then placed in an ultrasonic bath to disperse the particles. As soon as the mixture reached room temperature and had begun to thicken, it was poured in a 35×10 mm Petri dish and placed at 4° C. to complete the solidification process.

Silicone samples were prepared according to well known procedures in the art with the exception of the addition of fluorescent microspheres. These samples were also polymerized in Petri dishes to obtain a sample size of 35 mm in diameter by 10 mm thick. The reduced scattering and absorption coefficients of the samples were measured as 14 $cm^{-1}$ and 0.7 $cm^{-1}$ respectively at 806 nm by methods well known in the art.

For experiments on imaging of living cells in turbid media the samples were prepared as following: cell cultures MDA-MB-231 cell line stably expressing paxillin-EGFP were grown in high glucose DMEM medium (Gibco) supplemented with 10% heat-inactivated fetal bolvine serum (Invitrogen), 5 mM HEPES (Sigma), and 100 IU/ml penicillin/streptomycin (Invitrogen). Cells were cultured at 37° C. in a humidified 5% $CO_2$ atmosphere. Cells were resuspended to a final concentration of 5×$10^4$ cells/ml in type I collagen solution (final concentration of 2 mg/ml) in PBS, pH value was carefully adjusted with 1M NaOH to ~pH 7. 250 ul of cell-collagen solution was pipetted into one 8-well chambered coverglass (Lab-Tek), and kept at 20 C for 1 hour, then moved to 37° C. incubator for 1 hour before fresh medium was applied. The collagen gel containing cells (gel size ~10×10×1 mm thick) then was embedded in a larger size (35×10 mm Petri dish) scattering gel made of agar in PBS solution to which 0.3% of intralipid (Fresenius Kabi) was added as a scattering agent.

Figure 1:
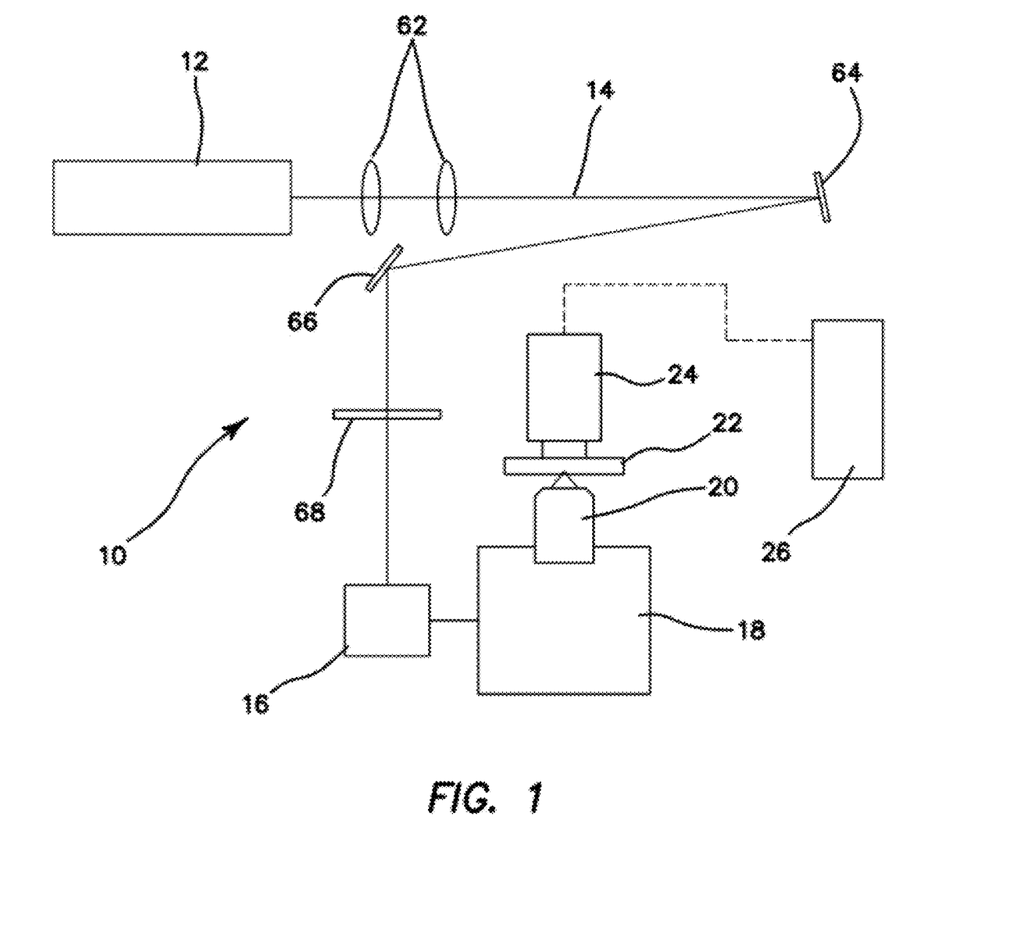
FIG. 1 is a schematic diagram of the current apparatus for light emission detection for in-depth imaging of turbid media.

The experimental system of the current invention is shown in FIG. 1 and is generally denoted by reference numeral 10. A femtosecond Ti:Sapphire laser 12 (Tsunami Spectra-Physics, 100 fs, 80 MHz, 800 nm) was used for the two-photon excitation of a sample 22. The laser 12 creates an excitation beam 14 which is directed through a beam expander 62 and then reflected off of a first mirror 64 and then a second mirror 66. The beam 14 then passes through a ND filters wheel 68 into an ISS Alba x-y scanner 16 coupled to a Nikon Eclipse TE2000-U microscope 18 equipped with a long working distance Olympus LCPlanFI 20×/0.4 air objective 20. The objective 20 was mounted on a piezo-stage to perform the z-scan. The maximum power of the excitation beam 14 reaching the sample 22 was about 160 mW. The turbid sample 22 in the Petri dish was placed on a microscope stage and the excitation beam 14 was focused by an objective lens inside the sample 22 from its bottom side. The two-photon induced fluorescence was collected by a detector 24 placed directly on top of the sample 22. To prevent external light from hitting the sensitive detector 24, the components were enclosed in a light-sealed box made out of black cardboard (not shown). The detector 24 is in turn coupled to a computer 26.

The detector 24 is the key feature of the described experimental setup. The detector 24 and the principle of its operation are shown schematically in FIG. 2A. The detector 24 consists of a head-on photomultiplier tube (PMT) with a 25 mm diameter photocathode 28 (Hamamatsu PMT R-1104) that operates in photon-counting mode. The PMT photocathode 28 is coupled to a glass cylinder 30 with mirror coated walls. The cylinder 30 works as a light-guide or waveguide to direct fluorescence photons 38 to the PMT photocathode 28. An optical shutter 36 coupled to the bottom of the glass cylinder 30 comprises two 25×3 mm optical filters 34 (Schott BG-39) that transmit fluorescence, but prevent excitation light from entering the PMT photocathode 28. There is a ~0.2 mm gap between filters 34 were a 0.1 mm thin aluminum plate 32 can be inserted to close the shutter 36. All the components of the detector 24 are connected with index matching compounds and the gap between filters 34 is filled with an index matching liquid to minimize losses of fluorescence photons 38 due to reflection at the boundaries. For the same purpose, during measurements the detector 24 was placed directly in contact with the surface of the sample 22.

Figures 2A, 2B:
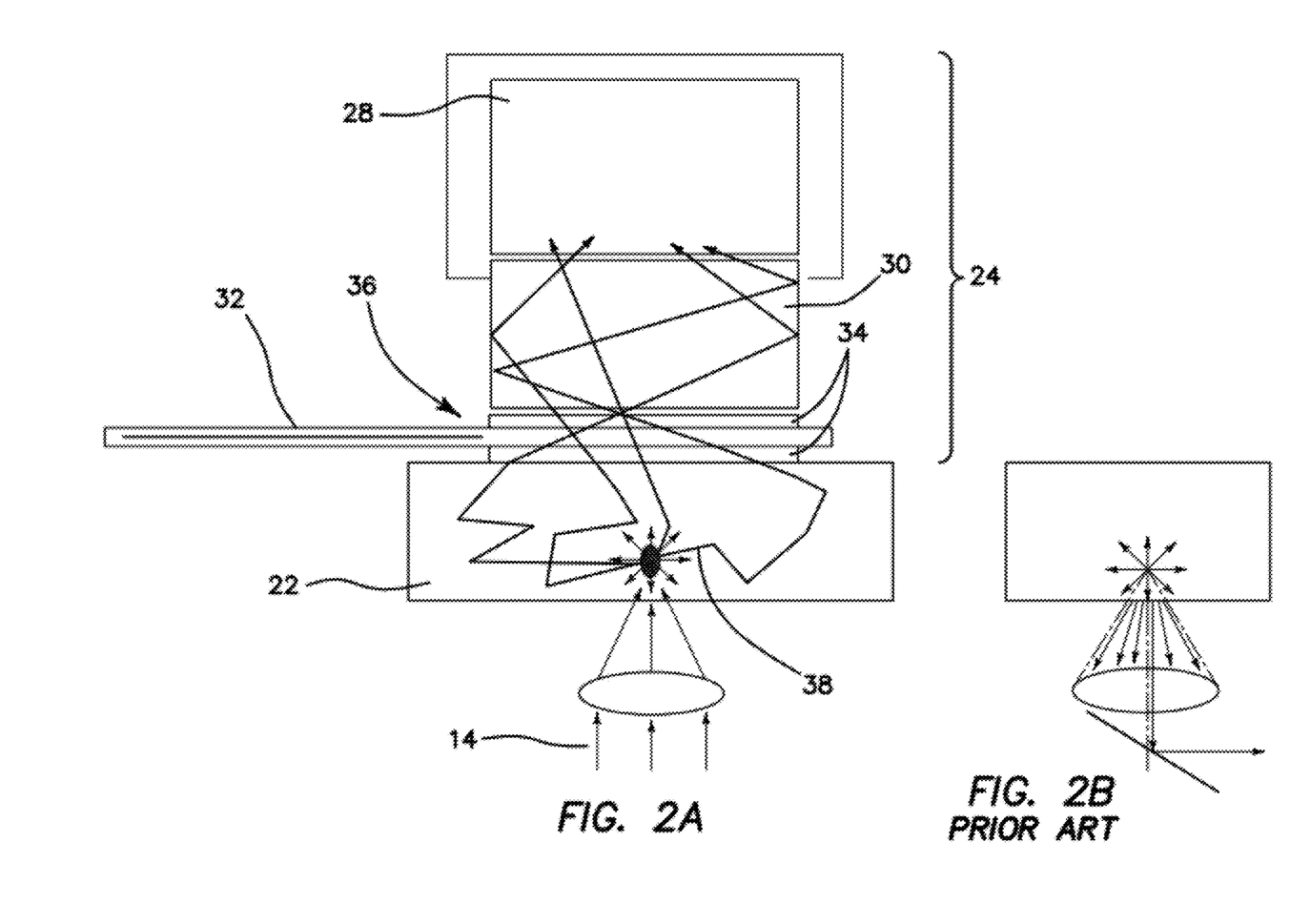
FIG. 2A is a magnified view of the detector portion of the apparatus seen in FIG. 1 disposed on top of a sample of turbid media.
FIG. 2B is a magnified frontal schematic view of an excitation beam of the prior art striking a sample of turbid media.

As shown in FIG. 2A, the two-photon induced fluorescence photons 38 of the excitation beam 14 are multiply-scattered inside the turbid sample 22 and when they reach the surface they are collected by the detector 24 from a wide surface area of 25 mm in diameter. Because of multiple scattering, photons 38 originally directed out of the detector 24 have the probability to be redirected and enter the detector 24. For the same reason, in the multiple scattering media, where photons 38 continuously change direction, light losses due to total internal reflection at the sample/detector boundary are reduced and fluorescence photons 38 that reach it can be picked up by the detector 24 from any angle of incidence. Theoretically, multiple scattering may even enhance fluorescence detection because in multiple scattering media the intensity of the scattered photons decays as 1/distance from the excitation light focus, which is slower than the 1/(distance)$^2$ decay that takes place in clear media. The currently described detection method is very efficient in harvesting photons and no microscope objective is capable of collecting photons 38 from such a wide area. For comparison, FIG. 2B shows a conventional prior art two-photon microscope diagram where fluorescence photons can be collected by a microscope objective only from a relatively small area and at narrow angle.

The detector 24 is very simple in construction, it does not require complex optics, and it is also efficient for clear media samples. To prove this concept we conducted the measurements described below.

Figure 3:
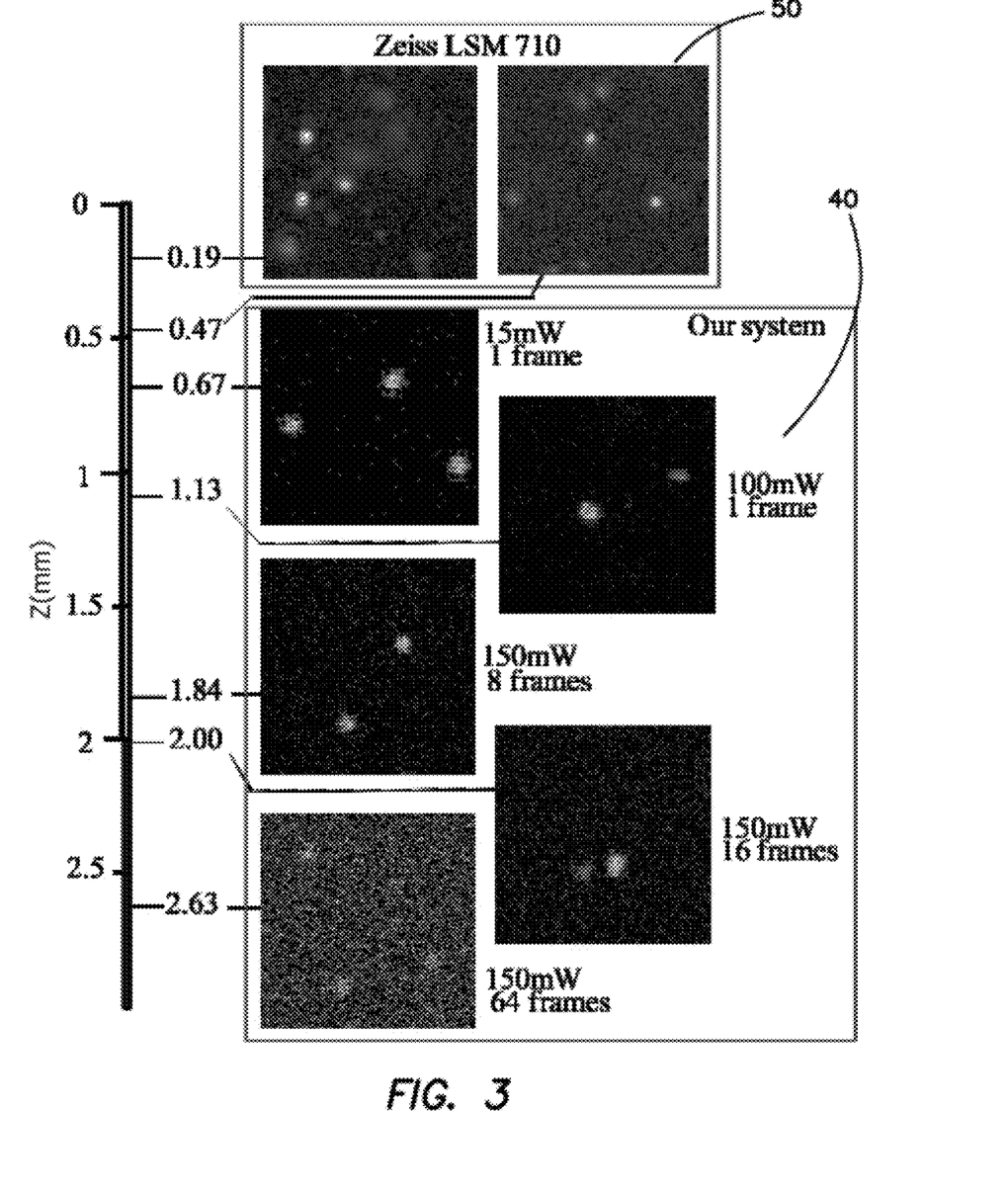
FIG. 3 is a series of images obtained by the apparatus seen in FIG. 1 at a variety of depths as indicated by the depth chart. Also seen is a set of images obtained by a related prior art method at the depth indicated by the depth chart.

FIG. 3 shows images of fluorescent beads dispersed in turbid samples and acquired at various depths shown by the depth chart located to left of the images. Similar results were obtained for samples made of gelatin or agar gel and silicone. It should also be known that other media now known or later devised other than what is listed here may also be used without departing from the original spirit and scope of the invention. It can be seen that with increased depth, i.e. the larger the z value given in the depth chart, the image intensity decays. Moreover, for deeper layers a higher excitation light power and more accumulated frames are required to maintain the image quality. Using the current system 10 and detector 24 we were able to obtain reasonable quality images of fluorescent beads at depths up to about 2.5 mm as seen within box 40 of FIG. 3. When the same samples were imaged with a commercial Zeiss LSM 710 two-photon fluorescence microscope with similar objective and excitation light power, the maximum imaging depth was about 0.5 mm as seen in box 50 within FIG. 3. 0.5 mm is in fact, the maximum imaging depth obtained so far in brain tissue, the optical properties of which we have replicated in our samples.

The images depicted in box 40 in FIG. 3 were acquired using an objective 20 with NA=0.4 (Olympus LCPlanFI 20×/0.4) for excitation. Because the beam 14 diameter at focus depends on the numerical aperture as $d=1.22\lambda/NA$, where $\lambda$ is a light wavelength, the use of higher NA objectives results in a smaller beam size, which in turn gives a higher excitation light intensity at focus and thus an increased imaging depth and resolution. However, high NA objectives usually have a short working distance. It has been shown that objectives with NA of 0.6-0.8 are optimal for two-photon imaging in turbid media. When an objective with NA=0.8 (Olympus LUMPlanFL/IR 40×/0.80 w) was used for excitation, it was possible to obtain high resolution images of fluorescent beads at a depth of 3 mm, which was limited mainly by the objective working distance.

Figure 4:
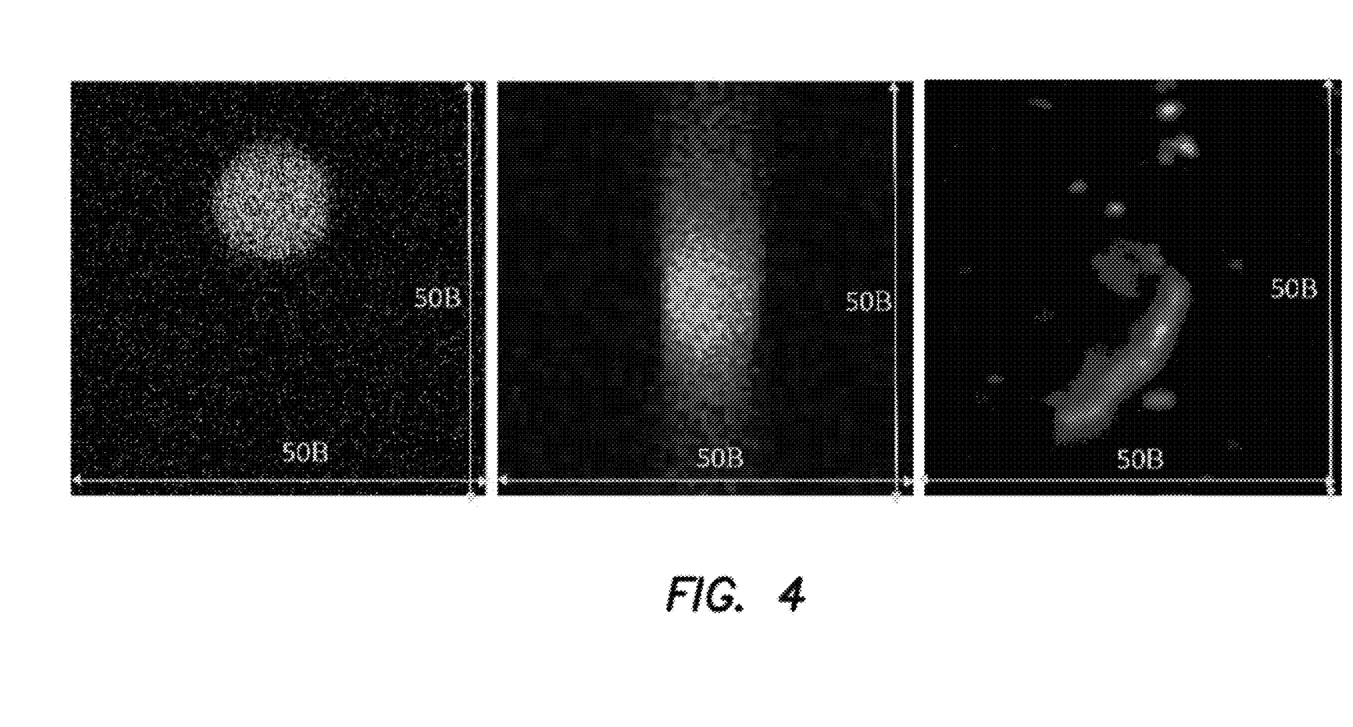
FIG. 4 is a series of images obtained by the apparatus seen in FIG. 1. The left panel is a x-y scan of a fluorescent sphere taken at a depth of 15 um, the middle panel is a x-z scan of the same sphere at the same depth, and the right panel is an image of a CHO-K1-GFP cell at a depth of 1 mm.

To verify the capability of the imaging system 10 to resolve fluorescent objects inside a turbid media, we performed imaging of samples containing 15 μm diameter fluorescent beads and CHO-K1-GFP cells embedded in a turbid gel. Cell solutions were sealed in ~150 μm diameter glass capillaries and then embedded in the turbid gel at various depths. FIG. 4 shows images of x-y and x-z scans of 15 μm fluorescent sphere and images of CHO-K1-GFP cells in the turbid gel at 1 mm depth. As shown in FIG. 4, the detector allows to image fluorescent objects inside a turbid gel at significant depths without loss of resolution.

Figure 5:
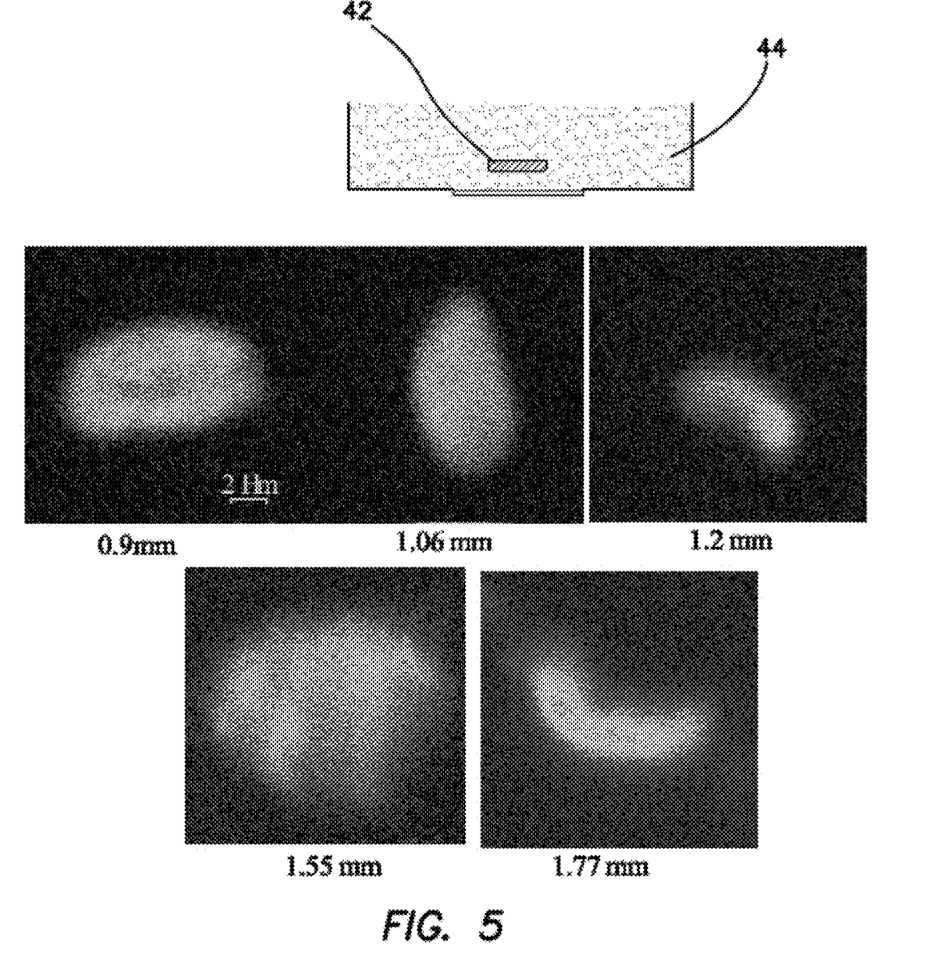
FIG. 5 is a series of images obtained by the apparatus seen in FIG. 1 of human breast cancer cells at a plurality of depths.

The results on imaging of living cells in turbid gel with optical properties imitating brain tissue are shown in FIG. 5. In these experiments we have used MDA-MB-231 human breast cancer cells 42 expressed with paxillin-EGFP and suspended in collagen gel. Because of collagen gel samples containing cells 42 were too small in size to take advantage of our detection system, they were enclosed in a bigger size scattering gel 44 and placed in a standard 35 mm Petri dish used for imaging with our detector 24. This surrounding scattering gel 44 was made of agar dissolved in hot PBS solution and then cooled to room temperature to become a gel. The intralipid solution was mixed with the liquid agar solution to induce scattering. The concentration of intralipid was adjusted to 0.3% to make a gel with the reduced scattering coefficient ~7 cm$^{-1}$. As is shown in FIG. 5, we were able to obtain high resolution images of these living cells 42 inside a turbid gel to a depth of approximately 2 mm.

It should be noted that fluorescence photons 38, induced at the excitation beam focus, have to travel through about 1 cm thickness of strongly scattering media before reaching the sample 22 surface, and yet they are efficiently detected with the current detection method.

To demonstrate the performance of the detection method, the experimental system utilizes an optical scheme where a two-photon excitation of fluorescence in thick turbid samples is applied to one side of the sample 22, while the detection of fluorescence is performed on its opposite side. Such schematics are not really suitable for a practical device meant for non-invasive imaging of deep tissue layers.

Figure 6:
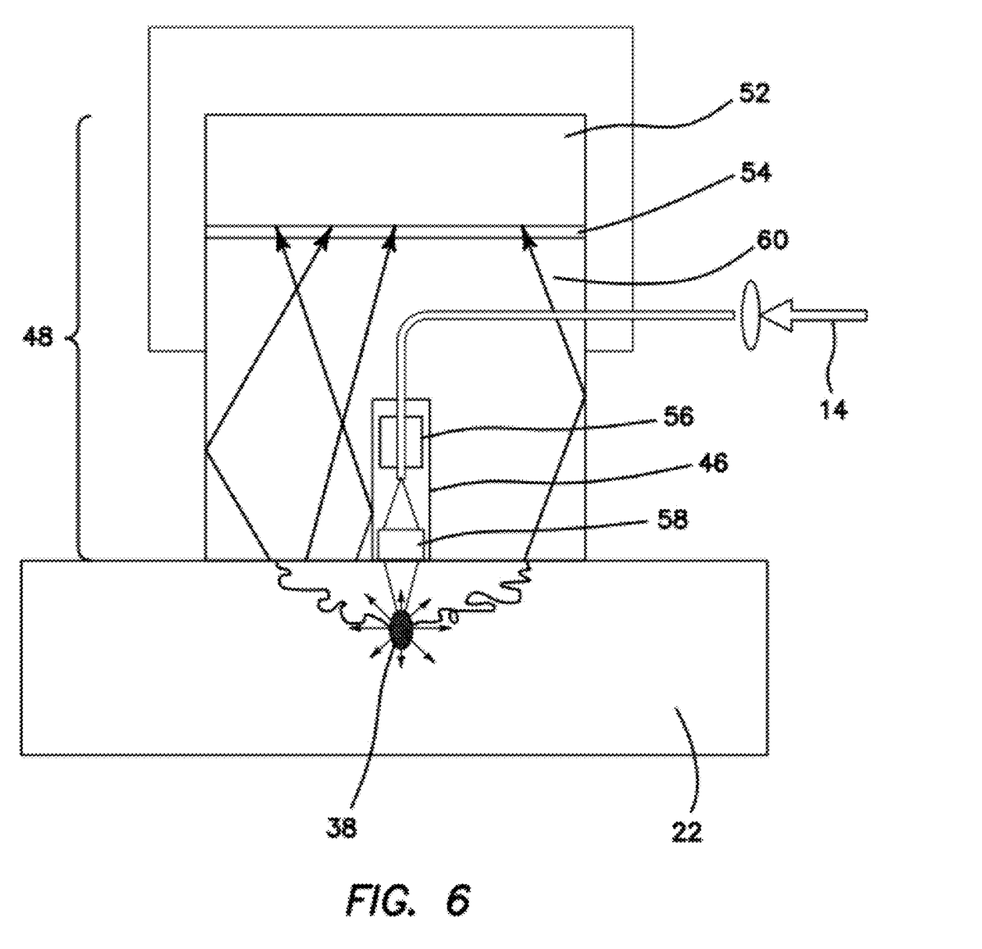
FIG. 6 is a magnified frontal schematic view of an alternative embodiment of the detector used in the apparatus seen in FIG. 1.

In a separate embodiment, optical schemes that combine fluorescence excitation optics with a wide area detector in a single unit can be realized according to the configuration shown in FIG. 6 with general reference numeral 48. This embodiment, like the previous embodiment described above, comprises a PMT photocathode 52 and a mirrored glass cylinder 60 directly disposed on top of the sample 22. A filter 54 is also disposed within the glass cylinder 60 filters the excitation light from the transmitted fluorescence before entering the PMT photocathode 52. In this scheme a scanning excitation device 46, such as a fiber optic scanning two-photon fluorescence endoscope which comprises a piezoelectric scanner 56 and a GRIN lens 58, can be embedded into the light guiding cylinder 60 of the detector 48. The excitation beam 14 enters the detector 48 through the scanning excitation device 46 and enters the sample 22. Scattered fluorescence photons 38 enter the glass cylinder 60 and then are directed towards the filter 54 and PMT photocathode 52. Because of the small size of the excitation device 46 (just a few millimeters in diameter), it will not significantly prevent fluorescence photons 38, which are collected from a much wider area, from reaching the photocathode 52 of the detector 48 and decrease its overall sensitivity.

In summary, the current fluorescence detection method that, in combination with a two-photon fluorescence scanning microscope 18, allows to image fluorescent objects inside tissue-like turbid media with micron scale resolution. The detector 24 collects photons 38 from the wide (25 mm diameter) area of the sample 22 with minimum photon losses, which makes it exceptionally sensitive to low light levels.

By using the detector 24 it is possible to increase imaging depth of turbid samples up to 3 mm, while other currently available state-of-the-art commercial two-photon fluorescence microscopes are only able to image the same samples at a maximum depth of 0.5 mm and the maximum reported imaging depth in similar samples does not exceed 1 mm. The imaging depth can be further enhanced by incorporating other methods targeting fluorescence excitation aspects.

The detector 24 is simple in construction and can potentially be utilized in devices for non-invasive imaging of a few millimeters deep tissue layers.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

We claim:

1. An apparatus for imaging in depth in a turbid sample comprising:
   a source of an excitation beam;
   excitation optics optically coupled to the excitation beam for optically processing the excitation beam;
   a microscope optically coupled with the processed excitation beam;
   an objective coupled to the microscope disposed on a first side of the turbid sample for directing the coupled excitation beam onto the first side of the turbid sample; and
   a detector assembly disposed on a second side of the turbid sample, wherein the detector includes detection optics, wherein the detector assembly further comprises:
- a mirror coated cylinder including a first end and a second end;
- a photomultiplier tube optically coupled with the first end of the mirror coated cylinder; and
- a shutter optically coupled with the second end of the cylinder, wherein the shutter further includes a plurality of filters and a selectively movable plate for opening and closing the shutter.

2. The apparatus of claim 1 where the means for producing an in depth image from detected fluorescence coupled to the detector comprises means for producing an image of fluorescence from approximately 1-3 mm deep within the turbid sample.

3. The apparatus of claim 1 where the excitation beam is directed from the objective disposed on the first side of the turbid sample and opposing the detector which is disposed on the second side of the turbid sample.

4. The apparatus of claim 1 where the detection optics of the detector is disposed directly onto the surface of the turbid sample.

5. The apparatus of claim 1 where the plate of the shutter is disposed between two filters.

6. The apparatus of claim 1 wherein the photomultiplier tube is a wide cathode area photomultiplier tube and is optically coupled to the mirror coated cylinder which functions as a waveguide and further including an index matching compound between the shutter, filters, mirror coated cylinder and photomultiplier tube photocathode.

7. The apparatus of claim 1 where at least a portion of the excitation optics are disposed within the detector assembly.

8. The apparatus of claim 7 where the portion of the excitation optics disposed within the detector assembly comprises: an optical fiber optically coupled to the objective and extending into the detector assembly; a piezoelectric scanner optically coupled to the optical fiber; and a GRIN lens optically coupled to the piezoelectric scanner, the GRIN lens arranged and configured within the detector assembly to be disposed onto the turbid sample.

9. The apparatus of claim 7 where the excitation optics comprises a piezoelectric scanner and a GRIN lens.

* * * * *